United States Patent [19]
Aino et al.

[11] Patent Number: 5,935,571
[45] Date of Patent: Aug. 10, 1999

[54] PLUG MIXTURE FOR RAISING SEEDLINGS AND METHOD FOR PRODUCING IT, AND METHOD FOR RAISING DISEASE TOLERANT SEEDLINGS

[75] Inventors: Masataka Aino, 1-5-7, Nakamachi, Sakuragaoka, Nishi-ku, Kobe-shi, Hyogo-ken; Yoshio Maekawa, Miki; Taizo Akiyama, Takasago; Yukihiko Yoshimi, Kakogawa, all of Japan

[73] Assignees: Taki Chemical Co., Ltd.; Masataka Aino, both of Japan

[21] Appl. No.: 08/810,802

[22] Filed: Mar. 6, 1997

[30] Foreign Application Priority Data

May 20, 1996 [JP] Japan ..................... 8-149988

[51] Int. Cl.$^6$ ............... A01N 63/00; C12N 1/20; C12N 5/00; C12P 21/04
[52] U.S. Cl. ............. 424/93.47; 435/71.3; 435/170; 435/252.4; 435/253.3; 435/420; 435/874; 435/876; 47/57.6
[58] Field of Search ............ 424/93.47; 435/170, 435/71.3, 240.4, 874–877, 243, 252.4, 253.3, 420; 47/57.6

[56] References Cited

U.S. PATENT DOCUMENTS

| | | | |
|---|---|---|---|
| 4,880,745 | 11/1989 | Kijima et al. | 424/93.47 |
| 4,948,413 | 8/1990 | Maekawa et al. | 504/117 |
| 5,348,742 | 9/1994 | Howell et al. | 424/93.47 |
| 5,496,547 | 3/1996 | Lam et al. | 424/93.47 |

FOREIGN PATENT DOCUMENTS

| | | |
|---|---|---|
| 0 294 053 | 12/1988 | European Pat. Off. . |
| 4-117278 | 4/1992 | Japan . |
| 5-068535 | 3/1993 | Japan . |
| 5-070316 | 3/1993 | Japan . |
| 7-163334 | 6/1995 | Japan . |
| 8-193017 | 7/1996 | Japan . |
| 8-268825 | 10/1996 | Japan . |
| 8-268826 | 10/1996 | Japan . |
| WO95/28085 | 10/1995 | WIPO . |

OTHER PUBLICATIONS

*Derwent Chemical Patents Index, Documentation Abstracts Journal*, Week 9534, Abstract No. AN 95–260030 (abstract of JP 07–163334) (Oct. 6, 1995).
Kloepper et al., *Trends in Biotechnology*, 7(2), 39–44 (1989).
Schroth et al., *Science*, 216, 1376–1381 (Jun. 25, 1982).
Keel et al., *Symbiosis*, 9, 327–341 (1990).

*Primary Examiner*—Leon B. Lankford, Jr.
*Assistant Examiner*—Christopher R. Tate
*Attorney, Agent, or Firm*—Wenderoth, Lind & Ponack, L.L.P.

[57] ABSTRACT

Herein provided is a plug mixture for raising seedlings, which contains endosymbiotic Pseudomonads mutualistically colonizing in endorhizosphere, *Pseudomnonas fluoresce*FPT-9601 and Pseudomonas sp. FPH-9601. Using the plug mixture, soil-borne diseases of crop plants and flowering plants can be prevented, and the producibility of such plants can be increased. The plug mixture contains said two Pseudomonads in an amount of not smaller than $10^5$ CFU/g each, and may contain 1-[3-(4-hydroxyphenyl) propanoyl]-2-piperidone in an amount of not smaller than 10 ppm. The two strains are separately added to different plug mixtures, which are then blended to give the intended plug mixture for raising seedlings. To this is optionally added 1-[3-(4-hydroxyphenyl)propanoyl]-2-piperidone. The plug mixture is effective for preventing soil-borne diseases, such as bacterial wilt, fusarium wilt and late blight, of various crop plants.

11 Claims, No Drawings

PLUG MIXTURE FOR RAISING SEEDLINGS AND METHOD FOR PRODUCING IT, AND METHOD FOR RAISING DISEASE TOLERANT SEEDLINGS

FIELD OF THE INVENTION

The present invention relates to a plug mixture for raising seedlings, and a method for producing it, and also a method for raising disease tolerant seedlings, and the object of the invention is to prevent soil-borne diseases of crop plants and flowering plants, thereby improving the producibility of field crops.

BACKGROUND OF THE INVENTION

The recent agricultural technology is, both at home and abroad, directed to environment-protecting agriculture, and it is desired to establish agricultural techniques that are gentle to ecology. Given the situation, it is an urgent necessity for us to take some measures to prevent soil-borne diseases in raising crop plants and also flowering plants, but there are known no agricultural chemicals that are effective for preventing such soil-borne diseases without polluting the environment, and it has been difficult to prevent soil-borne diseases.

Heretofore, in plant husbandry under structure or the like, large amounts of soil fumigants have been being used for soil disinfection in order to prevent soil-borne diseases to be caused by injuries in continuous cropping or the like, thereby ensuring the producibility therein.

However, such soil fumigants are problematic in that they have negative influences on ecology including human beings, and therefore could not be used in future. Accordingly, it is now an important theme in the art to develop any other materials that are gentle to ecology for preventing soil-borne diseases, in place of soil fumigants.

On the other hand, to promote the orientation toward environment-protecting agriculture, many attempts have been being made at the use of materials comprising microbes that grow in soil and produce therein antagonists (antifungals and antibacterials against phytopathogens) thereby to prevent soil-borne diseases. However, such microbial materials are problematic in that their applicability is limited, that the reproducibility of their effects is often poor, that their effects do not often last long, and that their use is often difficult.

Given the situation as above, we, the present inventors have been studying various measures for preventing soil-borne diseases by the use of various microbial materials. We have already disclosed a means of using fluorescent bacteria that grow in the endorhizosphere of crop plants for preventing soil-borne diseases (see Japanese Patent Application Laid-Open No. 7-163334).

In addition, we have already proposed seeds as treated with said fluorescent bacteria along with N-acyl-lactams, in order to ensure the prevention of soil-borne diseases of crop plants thereby promoting the growth of crop plants (see Japanese Patent Application No. 7-23515).

Further, we have already proposed a material for preventing bacterial wilt, which comprises fluorescent bacteria with the ability to produce crystalline 2,4-diacetylphloroglucinol and with no antibiotic tolerant, said bacteria being isolated essentially from the endorhizosphere of crop plants (see Japanese Patent Application No. 7-99628).

Moreover, we have already proposed a method for preventing bacterial wilt, which comprises using microbes with phenol tolerance and with no ability to produce antimicrobial materials, said microbes being isolated essentially from the endorhizosphere of crop plants (see Japanese Patent Application No. 7-99629).

We have confirmed that the above-mentioned fluorescent bacterial materials comprising fluorescent bacteria that grow in the endorhizosphere of crop plants are effective for preventing bacterial wilt of crop plants that are raised within the range of temperatures at which said fluorescent bacteria can grow. However, we have found that the materials could not satisfactorily exhibit their effects in plant husbandry under structure or the like where the temperature may be 40° C. or higher. Under such high-temperature conditions, the colonization of the fluorescent bacteria in the endorhizosphere of crop plants is greatly lowered, resulting in that the fluorescent bacteria could not satisfactorily exhibit their effects in crop fields where the degree of severity of bacterial wilt is high or in long-term cultivation of crop plants.

With the recent development in intensive agriculture for plant husbandry under structure, the frequency of soil-borne diseases is increasing. For example, composite diseases of bacterial diseases and fungal diseases are increasing. However, even in crop fields with such composite diseases, some plants can still grow well. We, the present inventors have specifically noted this fact and have further promoted our studies. Specifically, we have searched healthy plants that are growing around the plants having soil-borne diseases, for gram-negative bacteria which are presumed to have the highest compatibility with plant roots.

After having succeeded in finding out the intended gram-negative bacteria, we have screened them for selecting therefrom those capable of colonizing in the endorhizosphere of plants to exhibit their function of inhibiting or preventing soil-borne diseases such as bacterial wilt, and have obtained two strains capable of endosymbiotically and mutualistically colonizing in the endorhizosphere of plants of Solanaceae with high frequency. We have further studied the means of incubating said two strains and the means of applying them to crop fields, and as a result, have found that, when said two strains are introduced into the endorhizosphere of plant seedlings, then they endosymbiotically and mutualistically colonize not only in the endorhizosphere of plants of Solanaceae but also in that of plants of Cruciferae, strawberries, potatoes, carnations and others, and the seedlings growing endosymbiotically with said two strains exhibit strong resistance against bacterial and fungal soil-borne diseases. On the basis of these findings, we have completed the present invention.

SUMMARY OF THE INVENTION

Specifically, the present invention provides a plug mixture for raising seedlings, which comprises endosymbiotic Pseudomonads mutualistically colonizing in the endorhizosphere of plants, *Pseudomonas fluorescence* FPT-9601 and Pseudomonas sp. FPH-9601 (hereinafter referred to as endosymbiotic Pseudomonads), a method for producing said plug mixture, and a method for raising disease tolerant seedlings in said plug mixture.

Further, the present invention provides a plug mixture for raising seedling, which comprises said endosymbiotic Pseudomonads, *Pseudomonas fluorescence* FPT-9601 and Pseudomonas sp. FPH-9601, along with 1-[3-(4-hydroxyphenyl)propanoyl]-2-piperidone that is presumed to control the enzymatic system in plants, a method for producing said plug mixture, and a method for raising disease tolerant seedlings in said plug mixture.

The method for raising disease tolerant seedlings of the present invention uses said plug mixture containing said endosymbiotic Pseudomonads, *Pseudomonas fluorescence* FPT-9601 and Pseudomonas sp. FPH-9601, in which disease tolerant seedlings are raised in said plug mixture with said two strains having initially colonized in the endorhizosphere therein, and thereafter the colonies in the endorhizosphere are enlarged in crop fields with the growth of the plants therein. According to this method, the present invention is characterized in that it prevents soil-borne diseases, such as bacterial wilt, fusarium wilt and late blight, of crop plants, such as potatoes, green peppers, tomatoes, eggplants, strawberries, cabbages and carnations.

DETAILED DESCRIPTION OF THE INVENTION

Now, the plug mixture for raising seedlings of the present invention, the method for producing it, and the method for raising disease tolerant seedlings are described in detail hereinunder. The two strains for use in the present invention are characterized in that they are endosymbiotic Pseudomonads. Specifically, as will be referred to hereinafter, the two strains growing endosymbiotically can more easily penetrate into the endorhizosphere of plants in the germination-hastening stage and the seedling stage thereof than those growing singly, and immediately after having penetrated into the endorhizosphere of the plants in any of said stages, the two strains rapidly, endosymbiotically and synergistically grow together therein.

The individual activities of these endosymbiotic Pseudomonads, *Pseudomonas fluorescence* FPT-9601 (hereinafter referred to as Ps. FPT) and Pseudomonas sp. FPH-9601 (hereinafter referred to as Ps. FPH) are described in detail hereinunder.

According to the Bergey's Manual of Systematic Bacteriology, Volume 2, 1986, Ps. FPT is grouped in the group of *Pseudomonas fluorescens* Biotype IV in view of the taxonomical characteristics thereof to be mentioned hereinafter, and is characterized in that it produces an antibiotic, 2,4-diacetylphloroglucinol in crystals.

Specifically, Ps. FPT is of a type of psychrotrophic, oligotrophic bacteria having a high rate of inocula colonization in the endorhizosphere of crop plants of Solanaceae and Cruciferae. This strain exhibited, in the antimicrobial assay thereof in ordinary media, strong antimicrobial activities against phytopathogens for soil-borne diseases, such as pathogens for fusarium wilt, gram-positive bacteria and pathogens for bacteria wilt.

On the other hand, Ps. FPH is a strain similar to both *Pseudomonas chlororaphis* and *Pseudomonas fluorescens*, in view of the taxonomical characteristics thereof to be mentioned hereinafter, and is a type of psychrotrophic bacteria specifically having a high rate of inocula colonization in the endorhizosphere of crop plants of Solanaceae.

In addition, Ps. FPH is characterized in that it produces fluorescent slime. In its antimicrobial assay in ordinary media against phytopathogens for soil-borne diseases, this strain exhibited no antimicrobial activity at all against the phytopathogenic bacteria tested (pathogens for tomato bacterial wilt) and the phytopathogenic fungi tested (pathogens for Rizoctonia disease, pathogens J1 and J2 for tomato fusarium wilt, pathogens for tomato crown (foot) and root rot, pathogens for carnation fusarium wilt).

These endosymbiotic Pseudomonads, Ps. EPT and Ps. FPH were isolated from the endorhizosphere of tomatoes (of a variety of Kantaro Jr.) in a crop field having a soil-borne disease of tomato bacterial wilt in Aboshi-ku, Himeji-shi, Hyogo-ken, Japan.

The two strains have been deposited in the National Institute of Bioscience and Human-Technology, Agency of Industrial Science and Technology of Japan, under a microbe deposition code number FERM BP-5478 for Ps. FPT and a microbe deposition code number FERM BP-5479 for Ps. FPH.

Now, the taxonomical characteristics of the strain Ps. FPT are described in detail hereinunder.
a) Morphological Characteristics:
   Gram-negative rod, 0.5 to 1.0 μm×1.5 to 2.0 μm.
   Motility: motile by polar flagella.
   Endospores formation:
b) Growing Condition:
   This forms circular, flat and cream-colored colonies in a PDA medium in 3 to 4 days. (PDA medium: This is prepared by diluting 3 to 5-fold potato dextrose, followed by adding 1.5% agar thereto.)
c) Physiological Characteristics:
   This produces 2,4-diacetylphloroglucinol in crystals. Viability temperature: 15° C. to 35° C. (Cells of the strain flocculate at 37° C.)
   OF test (glucose oxidation/glucose fermentation test): oxidative.
   Cytochrome oxidase reaction: −/±. (This is minus (−) within a period of ordinary detection.)
   Nitrate reduction: denitrification.
   Indole production: −.
   $H_2S$ production: −.
   Acetoin production: +.
   Levan formation from sucrose: +.
   L-arginine dihydrolase: +.
   Urease: −.
   Gelatin liquefaction: +.
   α-glucosidase: −/±.
   β-glucosidase: ±/+.
   β-galactosidase: −.
   Acid production: from citric acid, glucose, sucrose, D-melibiose, L-arabinose. Carbon sources for growth: Glucose, L-arabinose, D-mannose, D-mannitol, N-acetyl-D-qlucosamine, potassium gluconate, n-capric acid, dl-malic acid, sodium citrate. Next, the taxonomical characteristics of the strain Ps. FPH are described in detail hereinunder.
a) Morphological Characteristics:
   Gram-negative rod, 0.2 to 0.5 μm×1.0 to 1.5 μm.
   Motility: Yes, motile by polar fragella. Endospore formation: −
Growing Condition:
   This forms circular, flat and cream-colored colonies in a PDA medium in 2 to 3 days.
c) Physiological Characteristics:
   Production of fluorescent slime: +. Viability temperature: 15° C. to 37° C.
   OF test (glucose oxidation/glucose fermentation test): −.
   Cytochrome oxidase: +.
   Nitrate reduction (for producing nitrites from nitrates): +.
   Indole production: −.

H₂S production: −.
Acetoin production: −.
Levan formation from sucrose: −.
L-arginine dihydrolase: −.
Urease: −.
Gelatin liquefaction: −.
α-glucosidase: −.
β-glucosidase: +.
β-galactosidase: −.
Acylamidase: +.
Acid production: from citric acid. Carbon sources for growth: Glucose, D-mannose, D-mannitol, N-acetyl-D-glucosamine, potassium gluconate, dl-malic acid, sodium citrate, phenyl acetate, ethanol.

Next referred to is a method for incubating Ps. FPT and Ps. FPH. Both Ps. FPT and Ps. FPH can be incubated in the same manner. For example, cells of the two strains are statically incubated in a liquid medium containing 0.8 g/liter of potato extract and 4 g/liter of glucose, at 25° C. for 2 weeks to obtain propagated cells of said two strains, Ps. FPT and Ps. FPH.

Next, hereinunder referred to in detail is the endosymbioticity of the two strains, Ps. FPT and Ps. FPH.

When cells of both the two strains, Ps. FPT and Ps. FPH are co-incubated in a medium, the growth of the cells of Ps. FPH is inhibited due to the microbicidal substances (2,4-diacetylphloroglucinol and its derivatives) to be produced by the cells of Ps. FPT. Accordingly, in ordinary media, the endosymbiotic, mutualistic colonization of the two strains is not allowable. Obviously, however, the two behave in different ways in the presence of plants.

Now, the endosymbioticity of the two strains in the presence of plants is referred to below.

Tomato seeds were seeded in a plug mixture as prepared by blending two culture media, one having cells of Ps. FPT as predominantly incubated therein and the other having cells of Ps. FPH as predominantly incubated therein, then germinated and raised to seedlings. Then, the condition of the colonization of the both inocula in the endorhizosphere of the raised seedlings was observed, resulting in that the rate of inocula colonization of the both strains incubated together was higher than that of each strain incubated singly.

Immediately after the penetration of the both strains into plants, the both strains endosymbiotically and mutualistically grow in both the stems just above the ground and in the main roots, while moving toward the tips of the roots with the growth of the plants thereby to enlarge the sites of the plants where they form their colonies. Four months after the transplantation of the plants in a crop field, the thus-enlarged sites of the plants where the two strains form their colonies reach the thin roots of the plants. This phenomenon can be easily confirmed by reisolating the colonies of the two strains from the endorhizosphere of the plants. The both strains form their colonies more actively in the endorhizosphere of the plants when they are together, than when they are singly. Thus, with the growth of the roots of the plants, the two strains enlarge the sites of the plants where they form their colonies. It is presumed that this endosymbiotic, mutualistic colonization of the two strains in plants will be greatly related to the activity of the two strains to prevent soil-borne diseases of plants.

Next referred to in detail is the method of the present invention for producing a plug mixture for raising seedlings.

First in the present invention, a plug mixture for raising seedlings is dry-sterilized at 100° C. or higher, more preferably from 160 C. to 200° C., for from 0.5 to 1 hour. The dry-sterilization at temperatures higher than 200° C. is not economical in view of the costs of the equipment and fuel needed.

The object of the dry-sterilization of the plug mixture is to exterminate microbes existing therein to thereby sterilize the plug mixture.

The plug mixture to be used is not specifically defined and may be any one having air permeability and moisture-holding ability. For this, preferred is a plug mixture to be prepared by mixing vermiculite or peat moss with loam and humic soil.

Next, cells of Ps. FPT and cells of Ps. FPH are separately inoculated into the thus-sterilized plug mixtures, and then incubated in a sterile room to have a cell concentration of $10^5$ colony-forming units (CFU)/g or higher. The incubation may be effected generally at from 15 to 30° C. for 3 weeks or longer.

The incubation shall be continued to attain said cell concentration of $10^5$ CFU/g or higher. This is because, if the cell concentration is lower than $10^5$ CFU/g, it takes too much time to attain the intended colonization of the cells in seedlings.

Next, both the plug mixtures are blended prior to seeding thereon. The ratio of the two plug mixtures to be blended shall be such that the cell concentration in each plug mixture is $10^5$ CFU/g or higher. This is because, if the cell concentration in each plug mixture is lower than $10^5$ CFU/g, it takes too much time to attain the intended colonization of the cells of the both strains in seedlings.

Now is referred to hereinunder a more preferred embodiment of the method for producing such a plug mixture for raising seedlings.

First, cells of the two strains are separately suspended in an aqueous solution of sodium alginate to have a cell concentration of $10^4$ cells/ml or higher, preferably $10^6$ cells/ml or higher.

The concentration of sodium alginate in the aqueous solution is preferably from 0.01 to 1% by weight. The resulting cell suspensions are separately added to and mixed with a dry-sterilized plug mixture in a ratio of from 20 to 30 v/v %. Through the mixing of the cell suspension with the dry-sterilized plug mixture, sodium alginate is substituted for the divalent cations existing on the surface of the plug mixture, thereby forming a water-insoluble film on the surface of the plug mixture. Then, the cells are immobilized onto the surface of the plug mixture along with the water-insoluble film, and propagate thereon.

The immobilization of the cells in the plug mixture shall be conducted separately for the two strains.

The object of the immobilization of the cells in the plug mixture is to prevent the cells from being moved due to watering and to efficiently attain the colonization of the cells in the endorhizosphere of seedlings.

In the present invention, the plug mixture comprising cells of the two strains that may be prepared according to the method mentioned hereinabove is used for raising disease tolerant seedlings of various crop plants.

We, the present inventors have found that the rate of inocula colonization of the strains in the endorhizosphere of seedlings is noticeably lowered at high temperatures, for example, in summer season. Therefore, we have further studied in order to overcome this problem, and have found that 1-[3-(4-hydroxyphenyl)propanoyl]-2-piperidone is extremely effective as a stimulatory agent for Pseudomonads on colonizing in the endorhizosphere.

Regarding the use of this stimulatory agent, it may be added to the above-mentioned plug mixture comprising cells of the two strains in an amount of 10 ppm or more, preferably from 50 to 200 ppm. If its amount is less than 10 ppm, the stimulatory agent could not exhibit its effect satisfactorily; but even if its amount is more than 200 ppm, the effect of the stimulatory agent is no more enhanced.

The addition of the stimulatory agent to the plug mixture results in increasing the rate of inocula colonization of the strains and even shortening the period of time needed for the inocula colonization of the strains, not only at ordinary temperature but also at high temperatures.

Seeds of a desired crop plant are seeded in the plug mixture thus prepared in the manner mentioned hereinabove, and raised therein, and thereafter the thus-raised seedlings are transplanted in a crop field. The method for raising the seeds in the plug mixture and the method of raising the seedlings in a crop field do not differ at all from any ordinary methods.

The soil-borne diseases against which the present invention is specifically effective are bacterial wilt, fusarium wilt and late blight, but these are not limitative.

The crop plants for which the present invention is specifically effective are those of Solanaceae, Cruciferae, Rosaceae and Caryophyllaceae, more concretely, potatoes, tomatoes, cucumbers, eggplants, green peppers, cabbages, strawberries, carnations and others. However, these are not limitative.

EMBODIMENTS OF THE INVENTION

Now, the present invention is described in more detail with reference to the following examples, in which % is all by weight unless otherwise specifically indicated.

EXAMPLE 1
Detection and Isolation of Strains of the Invention

Plants were collected along with the soil in the rhizosphere around them, and their roots were dipped in city water in a tank and washed therein to remove the soil. Their stems were also washed with water. Then, the roots were dipped in an aqueous solution of 0.005% aerosol OT and shaken therein to remove therefrom the substances as adhered onto the surfaces of the roots. The roots were further washed with sterilized water, then dipped in a solution of 80% ethanol and shaken therein for 1 minute. Next, ethanol as adhered onto the roots was removed with sterilized water, and the roots were dipped and shaken in an aqueous solution of 1% sodium hypochlorite for 10 minutes. Sodium hypochlorite as adhered onto the roots was removed with sterilized water, and the stems were cut off. The resulting roots were used as the sample in this experiment.

The sample was cut into pieces of about 1 cm long, and these pieces were put on a potato-dextrose-agar plate containing 5 mg/liter of crystal violet.

This agar plate was incubated at from 20 to 23° C. for about 2 weeks to form bacterial colonies thereon.

If cells of Ps. FPT exist in the sample, they form colonies and crystals (2,4-diacetylphloroglucinol) in the roots and around them. The 2,4-diacetylphloroglucinol crystals emit bluish white fluorescent light, when exposed to ultraviolet ray having a wavelength of 365 nm. Depending on the presence or absence of the colonies and the crystals, the presence or absence of Ps. FPT in the sample can be determined.

On the other hand, the presence or absence of Ps. FPH in the sample can be determined as follows. If fluorescent slime-producing colonies are formed on the agar plate, the colonies are replicated onto a King B agar plate containing 200 mg/liter of streptomycin, 100 mg/liter of sodium ampicillin and 100 mg/liter of nalidixic acid. If they still grow on the King B agar plate, the colonies are of Ps. FPH.

Unless otherwise specifically indicated, the strains, Ps. FPT and Ps. FPH were detected hereinunder according to the above-mentioned methods.

Seeds of a tomato plant (of a variety of Ohgata Fukuju) were dipped in a solution of 80% ethanol for 1 minute with gently stirring, and then taken out. These were dipped in an aqueous solution of 1% sodium hypochlorite for 10 minutes to thereby sterilize the surfaces of the seeds, and then washed with water. These seeds were seeded in culture vessels in an amount of 3 seeds/vessel, each culture vessel containing agar medium (with no sucrose added) of White in the lower part (having a depth of 6 cm), a sea sand layer in the middle part (having a depth of 0.5 cm), and an agar-agar medium in the upper part (having a depth of 1 cm).

After the seeding, the seeds were raised in a light-aerobic condition at 28° C. After the top of the roots that had rooted from the seeds reached the sea sand layer, a cell suspension of $10^8$ cells/ml of Ps. FPT in sterilized water and a cell suspension of $10^8$ cells/ml of Ps. FPH in sterilized water were applied onto the surface of the medium, either singly or as combined. The amount of each cell suspension applied singly was about 1 v/v % of the volume of the medium in the vessel, while the amount of each cell suspension applied together was about 0.5 v/v % of the same.

These were further raised in a light-aerobic condition at 25° C. for 3 days. Then, a cell suspension of $10^8$ cells/ml of a pathogen for bacterial wilt was applied onto the surface of the medium in each vessel, in an amount of about 2 v/v % of the volume of the medium therein.

After the inoculation of the cells of the pathogen for bacterial wilt, the seedlings were further raised in a light-aerobic condition at 30° C. Apart from these test vessels, sterilized water was applied to the vessels in the control group, in place of the cell suspension of Ps. FPT and/or the cell suspension of Ps. FPH, and the control seedlings were raised in the same manner as for the test seedlings.

These seedlings were raised for 4 weeks after the inoculation with the pathogenic cells, and the occurrence of bacterial wilt in these seedlings were investigated. In addition, the cells of Ps. FPT and Ps. FPH were re-isolated from the raised seedlings.

From these data thus measured, calculated were the rate of occurrence of bacterial wilt in the seedlings, the rate of inocula-colonized seedlings in the endorhizosphere, and the rate of inocula-colonized length of roots of the seedlings. The data thus obtained are shown in Table 1 below. The rate of occurrence of bacterial wilt in the seedlings (hereinafter referred to as the rate of occurrence), the rate of inocula-colonized seedlings in the endorhizosphere (hereinafter referred to as the rate of inocula-colonized seedlings), and the rate of inocula-colonized length of roots of the seedlings (hereinafter referred to as the rate of inocula-colonized length of roots) were calculated according to the following equations.

Rate of occurrence (%) =[(number of diseased seedlings)/(number of all tested seedlings)]×100

Rate of inocula-colonized seedlings (%) =[(number of seedlings from which cells Ps. FPT and/or Ps. FPH were re-isolated)/(number of all tested seedlings)]×100

Rate of inocula-colonized length of roots (%) =[(length of roots of seedlings from which cells of Ps. FPT and/or Ps. FPH were re-isolated)/(length of roots of all tested seedlings )]×100

(The length of roots of seedlings was measured according to the Marsh's lattice line method (in 1971), in which the total length of roots is determined by measuring the number of crossing points at lattice lines (5 mm×5 mm) in a counting plate.)

TABLE 1

| Test Group | Control | Ps. FPT | Ps. FPH | Mixture of Two Strains | |
|---|---|---|---|---|---|
| Heat of occurrence (%) | 89 | 22 | 11 | 0 | |
| Rate of inocula-colonized seedlings (%) | — | 78 | 89 | Ps. FPT<br>Ps. FPH | 89<br>100 |
| Rate of Inocula-colonized Length of Roots (%) | — | 15 | 33 | Ps. FPT<br>Ps. FPH | 38<br>48 |

EXAMPLE 2

A commercially-available plug mixture for cell-raised seedling systems (Metromix-350, trade name of the product of Scott Co. in USA) was dry-sterilized at 120° C. for 1 hour (the dry sterilization is hereinafter referred to as heat treatment). On the other hand, cells of Ps. FPT and cells of Ps. FPH were separately suspended in sterilized water to give cell suspensions of $10^9$ cells/ml each.

These cell suspensions were separately applied to the plug mixture each in an amount of 10 v/v % of the plug mixture. Thus were prepared a Ps. FPT-containing plug mixture and a Ps. FPH-containing plug mixture.

Apart from these, sterilized water was added to the heat-treated plug mixture in an amount of 10 v/v % of the plug mixture. This was used as the control plug mixture. In addition, the Ps. FPT-containing plug mixture and the Ps. FPH-containing plug mixture were blended in a ratio of 1/1 to prepare a blended plug mixture.

These four plug mixtures were separately filled in cell trays of a cell raised seedling system. Then, seeds of a tomato plant (of a variety of Momotaro), seeds of a green pepper plant (of a variety of Kyonami) and seeds of an eggplant (of a variety of Senryo No. 2) were seeded in each cell tray. The number of seedlings of each plant tested was 30.

After having been seeded, these were raised for 4 weeks in a controlled environment box in the cell raised seedling system. Then, the rate of inocula-colonized seedlings of each strain was obtained.

The data obtained are shown in Table 2 below.

TABLE 2

| | | Rate of Inocula-Colonized Seedlings(%) | | | | | |
|---|---|---|---|---|---|---|---|
| Plug Mixture Tested | Plant Tested | Tomato | | Green Pepper | | Eggplant | |
| | Strain Tested | Ps. FPT | Ps. FPH | Ps. FPT | Ps. FPH | Ps. FPT | Ps. FPH |
| Ps. FPT-containing Plug Mixture | | 17 | — | 13 | — | 7 | — |
| Ps. FPT-containing Plug Mixture | | — | 3 | — | 3 | — | — |
| Blended Plug Mixture | | 33 | 33 | 27 | 23 | 17 | 27 |
| Control Plug Mixture | | — | — | — | — | — | — |

Note:
In Table 2, "—" indicates that the density of the viable cells as measured according to the method mentioned above was below the level of re-isolation, and the same shall apply hereinunder.

EXAMPLE 3

Vermiculite, Red soils (a term of Japan soil classification) and a commercially-available plug mixture for raising seedlings (Taki Engei Baido; trade name of the product of Taki Chemical Co.) were blended in a ratio of 18/8/1, and heat-treated at 180° C. for 1 hour to prepare a plug mixture sample for raising seedlings. On the other hand, cells of Ps. FPT and cells of Ps. FPH were separately suspended in sterilized water to give cell suspensions of $10^2$ cells/ml, $10^3$ cells/ml, $10^4$ cells/ml, $10^5$ cells/ml, $10^6$ cells/ml, and $10^7$ cells/ml for each strain. Each cell suspension was added to the plug mixture sample in an amount of 20 v/v % of the sample, and statically left at 25° C. for 2 weeks. Apart from these, sterilized water was added to the heat-treated plug mixture sample in an amount of 20 v/v % of the sample, and statically left at 25° C. for 2 weeks. 10 g of each plug mixture sample as treated in the manner mentioned above was added to 100 ml of sterilized water, and shaken for 10 minutes. Then, the resulting supernatant was spread over a potato-dextrose-agar plate containing 5 mg/liter of crystal violet, and incubated thereon at 23° C. for 2 weeks. After the incubation, the colonies formed were measured, from which was obtained the number of survival of Ps. FPT and Ps. FPH in each sample. For the strain Ps. FPH, the number of survival thereof was obtained according to the replication method mentioned hereinabove.

The data of the number of survival thus obtained are shown in Table 3 below.

Next, the Ps. FPT-containing plug mixture and the Ps. FPH-containing plug mixture shown in Table 3 were blended in a ratio of 1/1 in different manners as indicated in Table 4 below. Using these blended samples, the test for raising seedlings of tomato, cabbage, white rape and Chinese cabbage was carried out in the same manner as in Example 2. The number of seedlings tested for each plant was 60. The data obtained are shown in Table 4.

TABLE 3

| No. of Cell-containing Plug Mixture Sample | Density of Inocula (cells/ml) | Number of Survival of Ps. FPT (CFU/g) | Number of Survival of Ps. FPH (CFU/g) |
|---|---|---|---|
| (1) Ps. FPT | $10^2$ | — | — |
| (2) Ps. FPT | $10^3$ | $10^2$ | — |
| (3) Ps. FPT | $10^4$ | $10^4$ | — |
| (4) Ps. FPT | $10^5$ | $10^6$ | — |
| (5) Ps. FPT | $10^6$ | $10^7$ | — |
| (6) Ps. FPT | $10^7$ | $10^8$ | — |
| (7) Ps. FPH | $10^2$ | — | — |
| (8) Ps. FPH | $10^3$ | — | $10^1$ |
| (9) Ps. FPH | $10^4$ | — | $10^2$ |
| (10) Ps. FPH | $10^5$ | — | $10^4$ |
| (11) PS. FPH | $10^6$ | — | $10^6$ |
| (12) PS. FPH | $10^7$ | — | $10^7$ |
| Control | Not inoculated | — | — |

TABLE 4

| Plant Tested Plug Mixture for Raising Seedlings (No. of Cell-containing Plug Mixture Sample) | | Rate of Inocula-Colonized Seedlings (%) | | | | | | | |
|---|---|---|---|---|---|---|---|---|---|
| | | Tomato | | Cabbage | | White Rape | | Chinese Cabbage | |
| | | PS. FPT | Ps. FPH | PS. FPT | Ps. FPH | PS. FPT | Ps. FPH | PS. FPT | Ps. FPH |
| Samples of the Invention | D:((4), (11)) | 53 | 58 | 50 | 52 | 52 | 62 | 40 | 57 |
| | E:((5), (12)) | 58 | 63 | 50 | 55 | 48 | 62 | 60 | 63 |
| Comparative Samples | Control | — | — | — | — | — | — | — | — |
| | A:((3), (12)) | 25 | 42 | 23 | 18 | 38 | 28 | 33 | 32 |
| | B:((4), (10)) | 13 | 25 | 13 | 5 | 17 | 8 | 22 | 13 |
| | C:((5), (10)) | 25 | 3 | 27 | 23 | 33 | 28 | 32 | 28 |

The plug mixture samples shown in Table 4 above were separately filled in cell trays of a cell raised seedling system. Then, seeds of a tomato plant (of a variety of House Momotaro) were seeded in each cell tray.

After having been seeded, these were raised for one week in a controlled environment box in the cell raised seedling system. Then, the seedlings were transferred into a glass house and further raised therein for 3 weeks still in the cell raised seedling system. These seedlings were transplanted in bacterial wilt-infected soil. The number of the seedlings was 30 for each group. Five weeks after the transplantation, the seedlings were observed to determine the resistance thereof to bacterial wilt.

The bacterial wilt-infected soil used herein had a pathogenic cell density of from $10^6$ to $10^7$ CFU/g.

The data obtained are shown in Table 5 below.

TABLE 5

| | Plug Mixture Tested | Rate of Occurrence (%) |
|---|---|---|
| Samples of the Invention | D | 37 |
| | E | 30 |
| Comparative Sample | Control | 90 |
| | A | 70 |
| | B | 77 |
| | C | 83 |

EXAMPLE 4

To each of the plug mixture samples D and E shown in Table 4 in Example 3, added was 1-[3-(4-hydroxyphenyl)propanoyl]-2-piperidone. Using these, the following tests for raising seedlings were carried out from the middle of July to the middle of August in 1995.

1-[3-(4-Hydroxyphenyl)propanoyl]-2-piperidone used herein was in the form of a mixture with silica powder comprising it in an amount of 10 w/w % of the silica powder. These plug mixture samples were separately filled in cell trays of a cell raised seedling system. Then, seeds of tomato plants (of varieties of Kantaro Jr., Merryroad and Momotaro) were seeded in each cell tray, as in Table 6 below.

After having been seeded, these were raised for one week in a controlled environment box in the cell raised seedling system. Then, the cell trays were transferred into a glass house, in which the raising was continued for further 2 weeks. The total period of time within which the temperature in the glass house was 30° C. or higher was about 200 hours.

The colonization of the inocula in the tomato seedlings was observed, and the rate of inocula-colonized seedlings of Ps. FPT and Ps. FPH in these seedlings was obtained. The data are shown in Table 6.

TABLE 6

| Type of Plug Mixture Used | Amount of HPP Added (ppm) | Rate of Inocula-Colonized Seedlings in Each Variety of Tomato Seedlings Tested (%) | | | | | |
|---|---|---|---|---|---|---|---|
| | | Merryroad | | Kantaro Jr. | | Momotaro | |
| | | Ps. FPT | Ps. FPH | Ps. FPT | Ps. FPH | Ps. FPT | Ps. FPH |
| D | Not added | 4 | 4 | 4 | 7 | 4 | 8 |
|   | 0.1 | 4 | 7 | 4 | 7 | 4 | 8 |
|   | 1 | 4 | 7 | 7 | 7 | 7 | 8 |
|   | 10 | 26 | 33 | 36 | 43 | 41 | 54 |
|   | 100 | 30 | 37 | 46 | 46 | 44 | 58 |
|   | 500 | 30 | 41 | 43 | 46 | 44 | 50 |
| E | Not added | 4 | 4 | 4 | 4 | 8 | 11 |
|   | 0.1 | 4 | 4 | 4 | 7 | 4 | 8 |
|   | 1 | 11 | 11 | 7 | 14 | 7 | 15 |
|   | 10 | 33 | 48 | 36 | 46 | 41 | 62 |
|   | 100 | 41 | 52 | 46 | 46 | 44 | 65 |
|   | 500 | 41 | 67 | 43 | 54 | 44 | 62 |

Note:
In Table 6, HPP is 1-[3-(4-hydroxyphenyl)propanoyl]-2-piperidone.

The data in Table 6 above indicate that the addition of HPP of 10 ppm or more significantly increased the rate of inocula-colonized seedlings in the tomato seedlings.

Using parts of the HPP-added plug mixture samples as prepared hereinabove and shown in Table 6, the following tests were carried out for raising tomato seedlings in bacterial wilt-infected soil.

The tests are as follows. The tomato seedlings that had been raised in the cell raised seedling system using any of the HPP-added plug mixture samples shown in Table 7 below were transplanted in the same bacterial wilt-infected soil as that used in Example 3. The number of the seedlings was 30 for each group. Five weeks after the transplantation, the seedlings were observed to determine the resistance thereof to bacterial wilt. The data obtained are shown in Table 7.

TABLE 7

| Plug Mixture Sample | Amount of HPP Added (ppm) | Rate of Occurrence of Bacterial Wilt (%) | | |
|---|---|---|---|---|
| | | Merryroad | Kantaro Jr. | Momotaro |
| D | 1 | 70 | 67 | 63 |
|   | 10 | 37 | 23 | 20 |
| E | 1 | 63 | 67 | 60 |
|   | 10 | 27 | 23 | 17 |

EXAMPLE 5

Vermiculite, Red soils (a term of Japan soil classification) and a commercially-available plug mixture for raising seedlings (trade name: Taki Engei Baido) were blended in a ratio of 10/4/1, and heat-treated at 80° C., 100° C. or 150° C. for 1 hour to prepare three different plug mixture samples, which were inoculated with cells of Ps. FPT or Ps. FPH in the manner mentioned below.

On the other hand, cells of Ps. FPT and cells of Ps. FPH were separately suspended in any of (1) sterilized water, (2) an aqueous solution of 0.01% sodium alginate and (3) an aqueous solution of 0.1% sodium alginate to prepare various cell suspensions having a cell density of $10^3$ cells/ml, $10^4$ cells/ml, $10^5$ cells/ml or $10^6$ cells/ml.

To each of the plug mixture samples prepared above, added was any of these cell suspensions in an amount of 20 v/v %, and blended. Thus were prepared herein 72 different cell-containing plug mixture samples in total. These were statically left at 25° C. for 2 weeks.

After having been thus left for 2 weeks, the number of survival of Ps. FPT and that of Ps. FPH in each plug mixture sample were counted. The data obtained are shown in Tables 8 and 9 below.

The plug mixture samples shown in Tables 8 and 9 were combined in a ratio of 1/1, as in Table 10, to prepare blended plug mixture samples. These were separately filled in cell trays of a cell raised seedling system. Then, seeds of a green pepper plant (of a variety of Kyoha) and seeds of an eggplant (of a variety of Senryo No. 2) were seeded in each cell tray. After having been seeded, these were raised for 5 weeks in a controlled environment box in the cell raised seedling system.

The seedlings thus raised were observed to determine the colonization of the inocula of Ps. FPT and Ps. FPH in these seedlings. The number of the seedlings tested herein was 30 for each group. Thus was obtained the rate of inocula-colonized seedlings of each strain. The data obtained are shown in Table 10 below.

TABLE 8

| No. of Plug Mixture Sample | Temperature for Heat Treatment | Type of Cell Suspension | Cell Density (cells/ml) | Number of Survival of Ps. FPT (CFU/g) |
|---|---|---|---|---|
| 01 | 80 | (1) | $10^3$ | — |
| 02 | 80 | (1) | $10^4$ | — |
| 03 | 80 | (1) | $10^5$ | — |
| 04 | 80 | (1) | $10^6$ | $10^4$ |
| 05 | 100 | (1) | $10^3$ | — |
| 06 | 100 | (1) | $10^4$ | — |
| 07 | 100 | (1) | $10^5$ | $10^4$ |
| 08 | 100 | (1) | $10^6$ | $10^6$ |
| 09 | 150 | (1) | $10^3$ | — |
| 10 | 150 | (1) | $10^4$ | $10^5$ |
| 11 | 150 | (1) | $10^5$ | $10^6$ |
| 12 | 150 | (1) | $10^6$ | $10^6$ |
| 13 | 80 | (2) | $10^3$ | — |
| 14 | 80 | (2) | $10^4$ | — |
| 15 | 80 | (2) | $10^5$ | $10^4$ |
| 16 | 80 | (2) | $10^6$ | $10^4$ |
| 17 | 100 | (2) | $10^3$ | $10^4$ |
| 18 | 100 | (2) | $10^4$ | $10^6$ |

TABLE 8-continued

| No. of Plug Mixture Sample | Temperature for Heat Treatment | Type of Cell Suspension | Cell Density (cells/ml) | Number of Survival of Ps. FPT (CFU/g) |
|---|---|---|---|---|
| 19 | 100 | (2) | $10^5$ | $10^6$ |
| 20 | 100 | (2) | $10^6$ | $10^7$ |
| 21 | 150 | (2) | $10^3$ | $10^5$ |
| 22 | 150 | (2) | $10^4$ | $10^6$ |
| 23 | 150 | (2) | $10^5$ | $10^7$ |
| 24 | 150 | (2) | $10^6$ | $10^8$ |
| 25 | 80 | (3) | $10^3$ | — |
| 26 | 80 | (3) | $10^4$ | — |
| 27 | 80 | (3) | $10^5$ | $10^4$ |
| 28 | 80 | (3) | $10^6$ | $10^5$ |
| 29 | 100 | (3) | $10^3$ | $10^4$ |
| 30 | 100 | (3) | $10^4$ | $10^6$ |
| 31 | 100 | (3) | $10^5$ | $10^7$ |
| 32 | 100 | (3) | $10^6$ | $10^8$ |
| 33 | 150 | (3) | $10^3$ | $10^5$ |
| 34 | 150 | (3) | $10^4$ | $10^6$ |
| 35 | 150 | (3) | $10^5$ | $10^7$ |
| 36 | 150 | (3) | $10^6$ | $10^8$ |

TABLE 9

| No. of Plug Mixture Sample | Temperature for Heat Treatment | Type of Cell Suspension | Cell Density (cells/ml) | Number of Survival of Ps. FPH (CFU/g) |
|---|---|---|---|---|
| 37 | 80 | (1) | $10^3$ | — |
| 38 | 80 | (1) | $10^4$ | — |
| 39 | 80 | (1) | $10^5$ | — |
| 40 | 80 | (1) | $10^6$ | — |
| 41 | 100 | (1) | $10^3$ | — |
| 42 | 100 | (1) | $10^4$ | — |
| 43 | 100 | (1) | $10^5$ | $10^5$ |
| 44 | 100 | (1) | $10^6$ | $10^6$ |
| 45 | 150 | (1) | $10^3$ | — |
| 46 | 150 | (1) | $10^4$ | $10^5$ |
| 47 | 150 | (1) | $10^5$ | $10^6$ |
| 48 | 150 | (1) | $10^6$ | $10^6$ |
| 49 | 80 | (2) | $10^3$ | — |
| 50 | 80 | (2) | $10^4$ | — |
| 51 | 80 | (2) | $10^5$ | — |
| 52 | 80 | (2) | $10^6$ | — |
| 53 | 100 | (2) | $10^3$ | — |
| 54 | 100 | (2) | $10^4$ | $10^5$ |
| 55 | 100 | (2) | $10^5$ | $10^6$ |
| 56 | 100 | (2) | $10^6$ | $10^6$ |
| 57 | 150 | (2) | $10^3$ | — |
| 58 | 150 | (2) | $10^4$ | $10^5$ |
| 59 | 150 | (2) | $10^5$ | $10^6$ |
| 60 | 150 | (2) | $10^6$ | $10^7$ |
| 61 | 80 | (3) | $10^3$ | — |
| 62 | 80 | (3) | $10^4$ | — |
| 63 | 80 | (3) | $10^5$ | — |
| 64 | 80 | (3) | $10^6$ | — |
| 65 | 100 | (3) | $10^3$ | $10^4$ |
| 66 | 100 | (3) | $10^4$ | $10^5$ |
| 67 | 100 | (3) | $10^5$ | $10^6$ |
| 68 | 100 | (3) | $10^6$ | $10^8$ |
| 69 | 150 | (3) | $10^3$ | $10^4$ |
| 70 | 150 | (3) | $10^4$ | $10^5$ |
| 71 | 150 | (3) | $10^5$ | $10^6$ |
| 72 | 150 | (3) | $10^6$ | $10^8$ |

As is obvious from the data in Tables 8 and 9, it is known that both Ps. FPT and Ps. FPH are extremely difficult to grow in the plug mixtures as heat-treated at temperatures lower than 100° C. It is also known that the addition of sodium alginate of 0.01% or more to the plug mixtures increased the number of survival of Ps. FPT and Ps. FPH in proportion to the concentration of sodium alginate added.

TABLE 10

| Code of Plug Mixture Sample | No. of Blended Plug Mixture Sample | Rate of Inocula-Colonized Seedlings (%) | | | |
|---|---|---|---|---|---|
| | | Raising of Eggplant Seedling | | Raising of Green Pepper Seedlings | |
| | | Ps. FPT | Ps. FPH | Ps. FPT | Ps. FPH |
| F | 07 | 46 | 7 | 13 | 10 | 13 |
| G | 11 | 47 | 30 | 37 | 50 | 37 |
| H | 18 | 55 | 27 | 40 | 43 | 60 |
| I | 28 | 60 | 7 | 10 | 17 | 10 |
| J | 36 | 72 | 47 | 53 | 80 | 87 |

As is obvious from the data in Table 10 above, it is known that the rate of inocula-colonized seedlings in the plug mixture samples of the invention, G, H and J is very high.

Next, the eggplant seedlings and the green pepper seedlings that had been raised for 5 weeks in the cell raised seedling system using any of the plug mixture samples F and J were transplanted in an eggplant fusarium wilt-infected field and a green pepper bacterial wilt-infected field, respectively, and were further raised therein for 3 months. The number of the seedlings of each plant transplanted was 60. The condition of the growth of these plants was observed, resulting in that the degree of prevention of the eggplant fusarium wilt was 8% in the sample F and 57% in the sample J and that the degree of prevention of the green pepper bacterial wilt was 25% in the sample F and 63% in the sample J.

EXAMPLE 6

Vermiculite, Red soils (a term of Japan soil classification) and a commercially-available plug mixture for raising seedlings (trade name: Taki Engei Baido) were blended in a ratio of 18/8/1, and heat-treated at 180° C. for 1 hour to prepare a plug mixture sample for raising seedlings. This was inoculated with cells of Ps. FPT and Ps. FPH in the manner mentioned below. On the other hand, cells of Ps. FPT and cells of Ps. FPH were separately suspended in an aqueous solution of 0.1% sodium alginate in an amount of $10^6$ cells/ml, to prepare cell suspensions.

These cell suspensions were separately added to the plug mixture sample that had been prepared in the above, in an amount of 20 v/v % of the sample, and statically left at 25° C. for 2 weeks. After having been thus left statically, the two samples were blended in a ratio of 1/1. Using the thus-blended plug mixture sample, the following tests were carried out for raising seedlings.

The blended plug mixture sample was filled in cell trays of a cell raised seedling system, and seeds of a tomato plant (of a variety of Momotaro 8), seeds of a green pepper plant (of a variety of Tosahime), seeds of an eggplant (of a variety of Ryoma) and seeds of a cabbage plant (of a variety of Aozora) were seeded in the cell trays, in which the plants were raised for from 4 to 8 weeks.

Apart from these, the following tests for raising strawberry, potato and carnation plants were carried out, using the same blended plug mixture sample as in the above under the conditions mentioned below.

For the test for raising the strawberry plant (of a variety of Hokowase), used were pots filled with the blended plug mixture, in which the lower parts of the runner plants that had grown from the runners were put on the blended plug mixture sample and the runner plants were made to root.

After the rooting, one part of the runner was wholly cut off from each runner plant, while the other part thereof was cut to still have a length of about 2 cm. These runner plants were implanted and fixed in the pots.

For the test for raising the potato plant (of a variety of Sanen), the blended plug mixture that had been prepared in the above was used to form about a half of the upper layer of each planting furrow (depth: about 15 cm) in a crop field, in which sprouted seed potato tubers were disposed. Then, these tubers were covered with the blended plug mixture at a thickness of about 8 cm, and raised.

For the test for raising the carnation plant, the panicles as cut off from the mother plant were implanted in flat boxes filled with the blended plug mixture that had been prepared in the above, and raised for about 30 days by fog culture.

After having been thus raised, the plants were observed to determine the rate of inocula-colonized seedlings in the endorhizosphere of each plant.

The number of the seedlings used in these tests was 30 for each plant. The data obtained are shown in Table 11 below.

TABLE 11

| Plant Tested | Rate of Inocula-Colonized Seedlings(%) | |
| --- | --- | --- |
| | Ps. FPT | Ps. FPH |
| Tomato | 53 | 83 |
| Green Pepper | 67 | 48 |
| Eggplant | 53 | 57 |
| Cabbage | 87 | 40 |
| Strawberry | 40 | 57 |
| Potato | 43 | 47 |
| Carnation | 67 | 53 |

The seedlings thus raised in the manner mentioned above were tested for the infection thereof with soil-borne diseases in crop fields of a farmer in Hyogo-ken, Japan. Precisely, the tomato seedlings were implanted in a bacterial wilt-infected field (for plant husbandry under structure), in a fusarium wilt-infected field (for plant husbandry under structure) and in a late blight-infected field (for plant husbandry under structure); the green pepper seedlings were implanted in a late blight-infected field (for plant husbandry under structure); the eggplant seedlings were implanted in a bacterial wilt-infected field (for plant husbandry under structure); the potato seedlings were implanted in a fusarium wilt-infected field (for plant husbandry in open air); and the strawberry seedlings and the carnation seedlings were planted in a fusarium wilt-infected field (for plant husbandry under structure) After having been raised in these fields, the plant seedlings were observed to determine the rate of occurrence of the disease of each seedling.

Apart from these, an aqueous solution of 0.1% sodium alginate was added to and mixed with the above-mentioned, heat-treated plug mixture. Using the resulting plug mixture as the control, the seedlings were raised in the same manner as above, and these were then implanted in the same fields as above, and observed to determine the degrees of their diseases.

The culture tests were repeated three times for each group of 20 seedlings. Except for the group of potato seedlings, the number of the diseased seedlings in each group was counted in one month starting from the time at which some seedlings in the control group were recognized to have been diseased. The data obtained are shown in Table 12 below.

TABLE 12

| Seedlings Tested | Type of Disease | Number of Diseased Seedlings in Control Group | Number of Diseased Seedlings in Test Group of the Invention |
| --- | --- | --- | --- |
| Tomato | Root rot | 15 | 0 |
| | Fusarium wilt | 23 | 1 |
| | Bacterial wilt | 36 | 5 |
| Green Pepper | Late blight | 16 | 3 |
| Eggplant | Bacterial wilt | 24 | 6 |
| Cabbage | Yellowing wilt | 11 | 2 |
| Strawberry | Yellowing wilt | 19 | 5 |
| Carnation | Fusarium wilt | 15 | 0 |
| Potato | Dry rot | 21 | 3 |

As has been described in detail hereinabove, the plug mixture of the present invention contains endosymbiotic Pseudomonads, Ps. FPT and Ps. FPH. Using the plug mixture of that type, disease tolerant seedlings having the both strains as colonized in the endorhizosphere thereof are raised, and then transplanted in crop fields where the colonies of the inocula as formed in the endorhizosphere of the plants are enlarged with the growth of the plants. According to this method of the present invention, the plug mixture of the invention exhibits excellent effects for preventing soil-borne diseases, such as bacterial wilt, fusarium wilt and late blight, of crop plants such as potatoes, green peppers, tomatoes, eggplants, strawberries, cabbages and carnations.

Where disease tolerant seedlings are raised with the plug mixture of the invention, the rate of inocula colonization of the strains in the endorhizosphere of the seedlings maybe often significantly lowered at high temperatures, for example, in summer season. However, if 1-[3-(4-hydroxyphenyl)propanoyl]-2-piperidone is added to the plug mixture as a stimulatory agent for Pseudomonads on colonizing in the endorhizosphere of plants, the rate of inocula colonization may be increased and even the period of time needed for the inocula colonization can be shortened, not only at ordinary temperature but also at high temperatures.

Thus, the plug mixture of the present invention is extremely effective for preventing soil-borne diseases of plants, where seedlings are implanted in crop fields in a high-temperature condition in which the rate of occurrence of soil-borne diseases of plants may be high, or are implanted in crop fields already infected with soil-borne diseases, or where the cultivation of plants in crop fields requires a long period of cultivation time.

While the invention has been described in detail and with reference to specific embodiments thereof, it will be apparent to one skilled in the art that various changes and modifications can be made therein without departing from the spirit and scope thereof.

What is claimed is:

1. A plug mixture for raising seedlings, which contains *Pseudomonas fluorescens* FPT-9601 (FERM BP-5478) and Pseudomonas sp. FPH-9601(FERM BP-5479), in an amount of not smaller than $10^5$ CFU/g each.

2. A plug mixture for raising seedlings, which contains *Pseudomonas fluorescens* FPT-9601 (FERM BP-5478) and Pseudomonas sp. FPH-9601 (FERM BP-5479), in an amount of not smaller than $10^5$ CFU/g each, and contains 1-[3-(4-hydroxyphenyl)propanoyl]-2-piperidone in an amount of about 10 to 200 ppm.

3. A method for producing a plug mixture for raising seedlings, which comprises separately inoculating

*Pseudomonas fluorescens* FPT-9601 (FERM BP-5478) and Pseudomonas sp. FPH-9601 (FERM BP-5479) into different plug mixtures, then incubating them to reach a cell density of not smaller than $10^5$ CFU/g each, and thereafter blending the resulting two plug mixtures in such a ratio that the resulting blend may contain the cells of the both strains in an amount of $10^5$ CFU/g each.

4. A method for producing a plug mixture for raising seedlings, which comprises separately inoculating *Pseudomonas fluorescens* FPT-9601 (FERM-BP5478) and Pseudomonas sp. FPH-9601 (FERM BP-5479) into different plug mixtures, then incubating them to reach a cell density of not smaller than $10^5$ CFU/g each, thereafter blending the resulting two plug mixtures in such a ratio that the resulting blend may contain the cells of the both strains in an amount of $10^5$ CFU/g each, and adding thereto 1-[3-(4-hydroxyphenyl)propanoyl]-2-piperidone in an amount of not smaller than 10 ppm.

5. The method for producing a plug mixture for raising seedlings as claimed in claim 3 or 4, wherein the inoculation *Pseudomonas fluorescens* FPT-9601 (FERM BP-5478) and Pseudomonas sp. FPH-9601 (FERM BP-5479) into different plug mixtures is effected by separately suspending the cells of the two strains in different aqueous solutions of sodium alginate in an amount of not smaller than $10^4$ cells/ml each, followed by separately adding the resulting cell suspensions to different plug mixtures and mixing them.

6. The method for producing a plug mixture for raising seedlings as claimed in claim 3 or 4 wherein said plug mixtures are heat-treated at temperatures not lower than 100° C. prior to being inoculated with said strains.

7. A method for raising disease tolerant seedlings, which comprises raising seedlings either by seeding seed in a plug mixture or by planting the seedlings in a plug mixture that contains *Pseudomonas fluorescens* FPT-9601 (FERM BP-5478) and Pseudomonas sp. FPH-9601(FERM BP-5479), in an amount of not smaller than $10^5$ CFU/g each.

8. A method for raising disease tolerant seedlings, which comprises raising seedlings either by planting seed in a plug mixture or by planting the seedlings in a plug mixture that contains *Pseudomonas fluorescens* FPT-9601 (FERM-BP 5478) and Pseudomonas sp. FPH-9601 (FERM BP-5479), in the amount of not smaller than $10^5$ CFU/g each, and contains 1-[3(4-hydroxyphenyl)propanoyl]-2-piperidone in an amount of about 10 to 200 ppm.

9. The method for raising disease tolerant seedlings as claimed in claim 7 or 8, wherein said seedlings to be raised with said plug mixture are those of potatoes, green peppers, tomatoes, eggplants, strawberries, cabbages or carnations.

10. The method for raising disease tolerant seedlings as claimed in claim 7 or 8, wherein said disease tolerant seedlings are tolerant of bacterial wilt, fusarium wilt or late blight.

11. The method for producing a plug mixture for raising seedlings as claimed in claim 5, wherein said plug mixtures are heat-treated at temperatures not lower than 100° C. prior to being inoculated with said strains.

* * * * *